United States Patent [19]

Jain

[11] Patent Number: 5,316,142
[45] Date of Patent: May 31, 1994

[54] SURGICAL NEEDLE AND PACKAGE COUNTER

[76] Inventor: Krishna M. Jain, 8405 Plover, Kalamazoo, Mich. 49002

[21] Appl. No.: 853,880

[22] Filed: Mar. 18, 1992

Related U.S. Application Data

[63] Continuation of Ser. No. 653,000, Feb. 8, 1991.

[51] Int. Cl.5 .............................................. A61B 17/02
[52] U.S. Cl. .................................. 206/370; 206/380; 206/63.3
[58] Field of Search .............. 206/363, 365, 366, 370, 206/380, 459.5, 63.3, 440, 438

[56] References Cited

U.S. PATENT DOCUMENTS

| | | | |
|---|---|---|---|
| 216,927 | 6/1879 | Wuensch | 206/380 X |
| 489,558 | 1/1893 | Essington | 206/380 X |
| 2,984,344 | 5/1961 | Weissman | 206/63.3 X |
| 3,926,234 | 12/1975 | Dean | 206/459 X |
| 4,090,606 | 5/1978 | Dawson | 206/459 X |
| 4,415,089 | 11/1983 | Ruffa | 206/63.3 X |
| 4,591,048 | 5/1986 | Eldridge, Jr. | 206/63.3 |
| 4,596,329 | 6/1986 | Eldridge, Jr. | 206/63.3 X |

Primary Examiner—Paul T. Sewell
Assistant Examiner—Jacob K. Ackun, Jr.
Attorney, Agent, or Firm—Varnum, Riddering, Schmidt & Howlett

[57] ABSTRACT

A surgical needle package counter is particularly constructed for receiving and snugly retaining an opened surgical needle package sequentially in a number of slots particularly configured and sized to receive such opened surgical needle packages. Each slot for receiving an opened surgical needle package is identified by a number with the numbers being in sequence so that an immediate total number of opened surgical needle packages stored in the counter may be observed. The surgical needle package counter may have an integral extension in which a foam filler or slab may be seated. The foam filler or slab is particularly formed to receive used surgical needles. Preferably, each used surgical needle will be received in a needle receiving zone which corresponds with the slot of the surgical needle package counter so that the number of used surgical needles can be automatically identified by the numerals which identify the surgical package slots. A suitable cover is provided for retaining the used surgical needles for disposal or possible future recount.

7 Claims, 1 Drawing Sheet 5,316,142

SURGICAL NEEDLE AND PACKAGE COUNTER

This is a continuation, of application Ser. No. 07/653,000, filed Feb. 8, 1991.

This invention relates in general to new and useful improvements in apparatus for counting surgical needles to make certain that all needles have been removed before closure, and more particularly to a surgical needle counter which includes a device for receiving used needle packages and thereby counting the number of needles utilized.

BACKGROUND OF THE INVENTION

During surgery, it is important to keep track of how many needles have been used to ensure that all of them have been removed from a patient when the operation is completed. Counting devices are frequently used in surgery to keep track of the number of used needles. It is also useful to keep track of the number of packages from which the needles have been dispensed so that a quick check of how many needles should be accounted for will provide a simple verification of the needle count, thereby facilitating needle control. Typically, the scrub nurse will simply stack the used needle packages on a tray for later counting. However, the needle packages are prone to become dislodged and lost on the floor of the operating room so that occasionally miscounts occur.

In the past, there have been developed suitable devices for counting used surgical needles. These are the subjects of U.S. Pat. No. 3,727,658 granted on Apr. 17, 1973 to John D. Eldridge, Jr.; U.S. Pat. No. 3,944,069 granted to John D. Eldridge, Jr. on May 16, 1976; U.S. Pat. No. 4,008,802 granted to Samuel L. Freitag on Feb. 22, 1977 and U.S. Pat. No. 4,243,140 granted to Robert H. Thrun on Jan. 6, 1981. There remains a need for an effective verification of the needle count.

SUMMARY OF THE INVENTION

In accordance with this invention, there has been developed a holder for used surgical needle packages, which holders are provided with means for receiving and retaining opened needle packages as an evidence of how many needles have been utilized. Such a holder is generally of a molded construction having a plurality of slots of a size and shape for tightly receiving an opened needle package. Each of the slots is numbered with the numbers being sequential so as to immediately identify the total number of needle packages utilized in a surgical procedure.

Also, in accordance with this invention, it is envisioned to either utilize prior needle counters of the type described above, or form as an integral part of the needle package counter a needle counter. Most particularly, it is proposed to provide the needle counter with means for receiving individual used needles in needle receiving zones which include indicia corresponding to the slots of the needle package counter so that any discrepancy in the number of needle packages utilized and the number of needles reclaimed is immediately visible.

With the above and other objects in view as will hereinafter appear, the nature of the invention will be more clearly understood by reference to the following detailed description, the appended claims, and the several views illustrated in the accompanying drawings.

DETAILED DESCRIPTION OF THE PREFERRED EMBODIMENT

Figure 1:
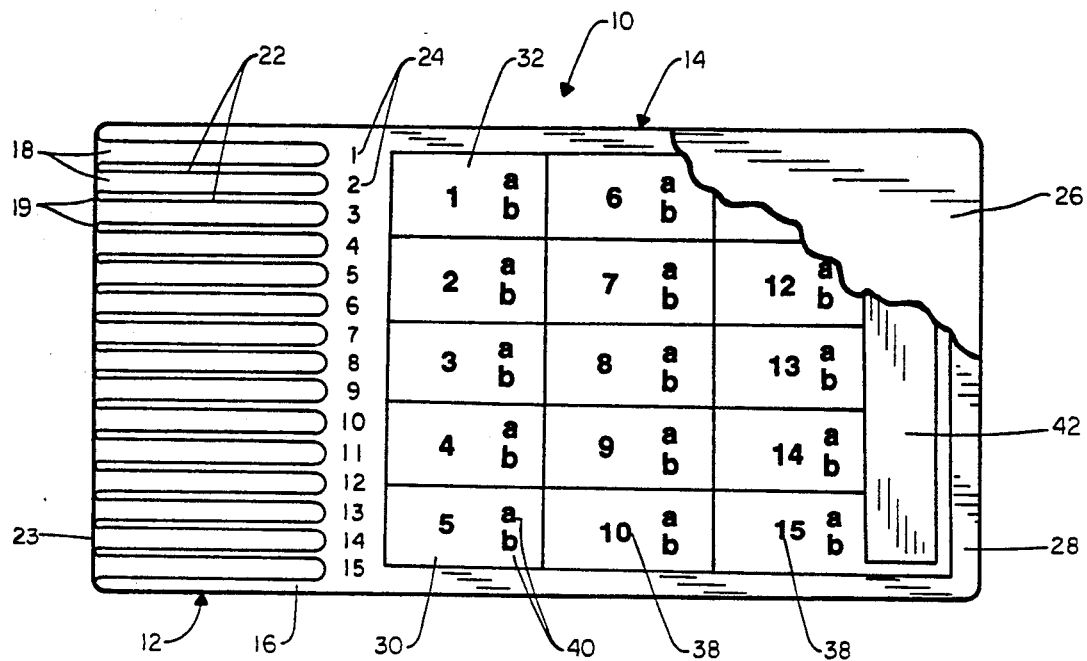
FIG. 1 is a plan view of a combined needle package counter and needle counter for surgical needles formed in accordance with this invention with a cover applied and portions of the cover being broken away so as to more specifically illustrate the use of the needle package counter.

Referring now to the drawings in detail, reference is made to the drawings wherein there is illustrated in FIG. 1 a combination surgical needle package counter and used surgical needle counter, generally identified by the numeral 10. The combined counter 10 includes a surgical needle package counter 12 and a surgical needle counter 14.

It is to be understood that the surgical needle package counter 12 may be utilized independently of the used surgical needle counter 14 and that any suitable surgical needle counter may be utilized including those specifically identified above.

Figure 2:
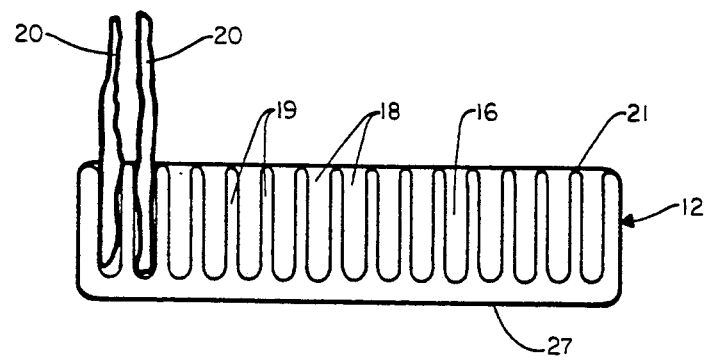
FIG. 2 is a front elevational view of the surgical needle package counter and surgical needle counter of FIG. 1 with parts broken away.

The surgical needle package counter 12 is in the form of a molded body forming a base 16 which is provided with a plurality of transversely extending slots 18 of a size to have snugly received therein an opened surgical needle package 20 as is best shown in FIG. 2. The slots 18 are defined by vertically disposed parallel panels 19. The panels 19 are in a rank extended across a substantial portion of an upper surface 21 of the base 16. In other words, this structure is comblike in appearance, with the panels 19 forming the teeth of the comb, and the slots 18 being defined by the interstices between the teeth. In order to facilitate the entry of an opened surgical needle package into an associated one of the slots 18, it is preferred that one end 22 of each slot open through an edge 23 of the base 16. At the opposite end of each of the slots 18, from the open end there is applied to the top of the base 16 numerals 24 which are arranged in sequence so as to immediately identify the total number of opened surgical needle packages and thus the total number of surgical needles utilized in a surgical procedure.

The base 16 is provided at one end thereof with a molded extension 28 formed integrally with the base 16. The extension 28 defines a cavity 30 in which there is seated a foam insert 32. The foam insert 32 will be provided with suitable means for receiving used needles. If desired, the foam insert 32 may be of a construction similar to the above-identified U.S. Pat. No. 4,008,802 and include a longitudinally extending, upstanding rib and a plurality of transversely extending slits or slots. The slits or slots will be of a size to snugly receive a used surgical needle, and each slit or slot may be aligned with one of the slots 18. Alternatively, the foam insert 32 can provide a simple flat surface, the foam being adapted to receive needles. Preferably, as shown in FIG. 1, the foam 32 is divided into needle receiving zones wherein primary indicia 38 are provided which correspond numerically to the numerals 24 on the base 16. In this manner, an immediate count of surgical needles used or otherwise accounted for can be readily verified by comparison with the number of used packages. For those frequent situations where a single package contains multiple needles, secondary indicia 40 may correspond to each individual needle. It can be seen that if the number of used surgical needles accounted for does not correspond with the correct number of opened surgical needle packages, the difference in number will be immediately observable and appropriate steps taken to ensure patient care.

A magnetic strip 42 is provided within the cavity 30 to receive and hold blades and sharps. The base 16 is provided with a suitable cover 26 so as to completely enclose the base 16 and thus prevent the loss of used surgical needles and blades. The cover can also facilitate easy disposal of the entire assembly and used needles and blades at the conclusion of surgery.

It is proposed that the surgical needle package counter 12 and the surgical needle counter be readily removably mounted adjacent the operating table. Accordingly, the underside of the base 16 is provided with a layer of adhesive 27 which will preferably be of the pressure-sensitive type with a removable cover.

Although only a preferred embodiment of the surgical needle package counter and the used surgical needle counter has been specifically illustrated and described herein, minor variations may be made in the construction thereof without departing from the spirit and scope of the invention as defined by the appended claims. For example, a magnetic insert may be substituted for the foam insert 32.

The embodiments of the invention in which an exclusive property or privilege is claimed are defined as follows:

1. A surgical needle package counter comprising a body having an upper surface and an adjoining side surface, at least one slot in said body, said at least one slot extending through said upper and side surfaces and adapted to receive a used needle package, said body further comprising a needle counting extension having means for receiving needles, said needle receiving means comprising a resilient flexible material disposed on the extension and having at least one needle receiving zone, a first visual indicium on said upper surface adjacent to said at least one slot for counting and identifying a used needle package received in said slot, a second visual indicium disposed on said needle receiving zone, said zone corresponding to said at least one slot by an identity between said first and second visual indicia so that needles received in the zone can be identified as coming from said used needle package in said at least one slot adjacent to the corresponding first visual indicium.

2. A surgical needle package counter according to claim 1 wherein said needle receiving zone includes a third indicium disposed thereon to identify each needle received in the zone.

3. A surgical needle package counter comprising a body having an upper surface and an adjoining side surface, at least one slot in said body, said at least one slot extending through said upper and side surfaces and adapted to receive a used needle package, said body having a needle counting extension with means for receiving used needles, said needle counting extension comprising a magnetized surface on the extension and having at least one needle receiving zone, a first visual indicium on said upper surface adjacent to said at least one slot for counting and identifying a used needle package received in said slot, a second visual indicium disposed on said needle receiving zone, said zone corresponding to said slot by an identity between said first and second visual indicia so that needles received in the zone can be identified as coming from said used needle package received in said at least one slot adjacent to the corresponding first visual indicium.

4. A surgical needle package counter according to claim 3 wherein said needle receiving zone includes a third indicium disposed thereon to identify each needle received in the zone.

5. A surgical needle package counter comprising a body having a comblike portion, said comblike portion having a plurality of teeth with interstices between the teeth for receiving and retaining used needle packages opened during surgery, said body further comprising a recessed portion having a surface, a plurality of needle receiving zones on the surface adapted to receive an retain needles, a unique visual indicium disposed on the body adjacent to each interstice for counting and identifying a used needle package received therein, the combination of needle counting indicia forming a first set of indicia, a visual indicium disposed on each needle receiving zone forming a second set of indicia, each zone corresponding to an interstice by an identity a particular one of between the first and a particular one of the second set of visual indicia so that needles received in a zone can be identified as coming from a needle package received in the interstice adjacent to a corresponding first visual indicium.

6. A surgical needle package counter according to claim 5 wherein said needle receiving zone includes a third indicium disposed thereon to identify each needle received in the zone.

7. A surgical needle package counter according to claim 6 further comprising a cover whereby needle packages and needles received by the body can be enclosed by the cover.

* * * * *